United States Patent
McCaffrey et al.

(10) Patent No.: US 10,201,284 B2
(45) Date of Patent: Feb. 12, 2019

(54) PRESSURE MEASURING CATHETER HAVING REDUCED ERROR FROM BENDING STRESSES

(71) Applicant: Medtronic Vascular, Inc., Santa Rosa, CA (US)

(72) Inventors: Gerry McCaffrey, Ballybrit (IE); Fiachra Sweeney, Ballybrit (IE); Christopher Murphy, Ballybrit (IE)

(73) Assignee: MEDTRONIC VASCULAR INC., Santa Rosa, CA (US)

( * ) Notice: Subject to any disclaimer, the term of this patent is extended or adjusted under 35 U.S.C. 154(b) by 853 days.

(21) Appl. No.: 14/595,884

(22) Filed: Jan. 13, 2015

(65) Prior Publication Data
US 2015/0359438 A1 Dec. 17, 2015

Related U.S. Application Data

(60) Provisional application No. 62/012,628, filed on Jun. 16, 2014.

(51) Int. Cl.
*A61B 5/0215* (2006.01)
*A61B 5/02* (2006.01)
*A61B 5/00* (2006.01)

(52) U.S. Cl.
CPC ........ *A61B 5/0215* (2013.01); *A61B 5/02007* (2013.01); *A61B 5/6852* (2013.01); *A61B 2562/0247* (2013.01)

(58) Field of Classification Search
CPC . A61B 5/0215; A61B 5/6852; A61B 5/02007; A61B 2562/0247
See application file for complete search history.

(56) References Cited

U.S. PATENT DOCUMENTS

| | | | |
|---|---|---|---|
| 4,718,425 A | 1/1988 | Tanaka et al. | |
| 4,771,782 A | 9/1988 | Millar | |
| 4,796,641 A | 1/1989 | Mills | |
| 4,815,472 A | 3/1989 | Wise | |
| 4,850,358 A | 7/1989 | Millar | |

(Continued)

FOREIGN PATENT DOCUMENTS

| | | |
|---|---|---|
| DE | 102008045878 | 3/2010 |
| EP | 0263190 | 10/1986 |

(Continued)

OTHER PUBLICATIONS

PCT/US2015/057058, The International Search Report and the Written Opinion of the International Searching Authority.

(Continued)

*Primary Examiner* — Tiffany Weston
*Assistant Examiner* — Tho Tran
(74) *Attorney, Agent, or Firm* — Medler Ferro Woodhouse & Mills PLLC

(57) ABSTRACT

Bending stresses experienced by a pressure sensor mounted to a fractional flow reserve catheter when tracking the catheter through the vasculature creates a distortion of the sensor resulting in an incorrect pressure reading or bend error. In order to isolate the sensor from bending stresses, the sensor is mounted with one end coupled to the distal end of the shaft while the other end of the sensor is not coupled to the catheter so that a portion of the sensor is spaced apart from the distal end of the shaft.

5 Claims, 11 Drawing Sheets

(56) References Cited

U.S. PATENT DOCUMENTS

| | | |
|---|---|---|
| 4,901,731 A | 2/1990 | Millar |
| 4,924,877 A | 5/1990 | Brooks |
| 4,928,693 A | 5/1990 | Goodin |
| 4,936,310 A | 6/1990 | Engstrom et al. |
| 4,941,473 A | 7/1990 | Tenerz et al. |
| 4,966,148 A | 10/1990 | Millar |
| 4,966,156 A | 10/1990 | Perry et al. |
| 5,029,585 A | 7/1991 | Lieber et al. |
| 5,046,497 A | 9/1991 | Millar |
| 5,050,297 A | 9/1991 | Metzger |
| 5,085,223 A | 2/1992 | Lars et al. |
| 5,125,058 A | 6/1992 | Tenerz et al. |
| 5,195,375 A | 3/1993 | Tenerz et al. |
| 5,267,958 A | 12/1993 | Buchbinder et al. |
| 5,280,786 A | 1/1994 | Wlodarczyk et al. |
| 5,427,114 A | 6/1995 | Colliver et al. |
| 5,451,233 A | 9/1995 | Yock |
| 5,466,222 A | 11/1995 | Ressemann et al. |
| 5,526,820 A | 6/1996 | Khoury |
| 5,542,434 A | 8/1996 | Imran et al. |
| 5,564,425 A | 10/1996 | Tonokura |
| 5,569,219 A | 10/1996 | Hakki et al. |
| 5,573,007 A | 11/1996 | Bobo, Sr. |
| 5,591,129 A | 1/1997 | Shoup et al. |
| 5,637,091 A | 6/1997 | Hakky et al. |
| RE35,648 E | 11/1997 | Tenerz et al. |
| 5,694,946 A | 12/1997 | Tenerz et al. |
| 5,701,905 A | 12/1997 | Esch |
| 5,715,827 A | 2/1998 | Corl et al. |
| 5,813,997 A | 9/1998 | Imran et al. |
| 5,827,243 A | 10/1998 | Palestrant |
| 5,873,835 A | 2/1999 | Hastings |
| 5,902,248 A | 5/1999 | Millar et al. |
| 5,964,714 A | 10/1999 | Lafontaine |
| 6,033,366 A | 3/2000 | Brockway |
| 6,056,719 A | 5/2000 | Mickley |
| 6,089,103 A | 7/2000 | Smith |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A | 11/2000 | Hammarstrom et al. |
| 6,167,763 B1 | 1/2001 | Tenerz et al. |
| 6,182,513 B1 | 2/2001 | Stemme et al. |
| 6,193,669 B1 | 2/2001 | Degany |
| 6,224,585 B1 | 5/2001 | Pfeiffer |
| 6,248,083 B1 | 6/2001 | Smith et al. |
| 6,296,615 B1 | 10/2001 | Brockway et al. |
| 6,312,380 B1 | 10/2001 | Brockway et al. |
| 6,336,906 B1 | 1/2002 | Hammarstrom et al. |
| 6,354,999 B1 | 3/2002 | Dgany |
| 6,379,308 B1 | 4/2002 | Brockway |
| 6,394,986 B1 | 5/2002 | Millar |
| 6,409,677 B1 | 6/2002 | Tulkki |
| 6,471,656 B1 | 10/2002 | Shalman et al. |
| 6,517,481 B2 | 2/2003 | Hoek et al. |
| 6,546,804 B2 | 4/2003 | Stemme et al. |
| 6,551,250 B2 | 4/2003 | Khalil |
| 6,565,514 B2 | 5/2003 | Svanerudh et al. |
| 6,585,660 B2 | 7/2003 | Dorando et al. |
| 6,615,067 B2 | 9/2003 | Hoek et al. |
| 6,615,667 B2 | 9/2003 | Smith |
| 6,659,957 B1 | 12/2003 | Vardi et al. |
| 6,659,959 B2 | 12/2003 | Brockway et al. |
| 6,663,570 B2 | 12/2003 | Mott et al. |
| 6,716,178 B1 | 4/2004 | Kilpatrick et al. |
| 6,733,459 B1 | 5/2004 | Atsumi |
| 6,754,608 B2 | 6/2004 | Svanrudh et al. |
| 6,767,327 B1 | 7/2004 | Corl et al. |
| 6,821,287 B1 | 11/2004 | Jang |
| 6,868,736 B2 | 3/2005 | Sawatari et al. |
| 6,926,674 B2 | 8/2005 | Tenerz et al. |
| 6,938,474 B2 | 9/2005 | Melvas |
| 6,966,890 B2 | 11/2005 | Coyle et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,017,416 B1 | 3/2006 | Liu et al. |
| 7,021,152 B2 | 4/2006 | Tenerz |
| 7,025,727 B2 | 4/2006 | Brockway |
| 7,060,038 B2 | 6/2006 | Letort et al. |
| 7,097,620 B2 | 8/2006 | Corl et al. |
| 7,112,170 B2 | 9/2006 | Schock et al. |
| 7,134,994 B2 | 11/2006 | Alpert et al. |
| 7,137,953 B2 | 11/2006 | Eigler et al. |
| 7,211,048 B1 | 5/2007 | Najafi |
| 7,222,539 B2 | 5/2007 | Tulkki |
| 7,229,403 B2 | 6/2007 | Schock |
| 7,245,789 B2 | 7/2007 | Bates et al. |
| 7,263,894 B2 | 9/2007 | Tenerz |
| 7,274,956 B2 | 9/2007 | Mott et al. |
| RE39,863 E | 10/2007 | Smith |
| 7,294,117 B2 | 11/2007 | Provost-tine et al. |
| 7,329,223 B1 | 2/2008 | Ainsworth et al. |
| 7,331,236 B2 | 2/2008 | Smith et al. |
| 7,343,811 B2 | 3/2008 | Tenerz et al. |
| 7,347,822 B2 | 3/2008 | Brockway |
| 7,447,388 B2 | 11/2008 | Bates et al. |
| 7,450,989 B2 | 11/2008 | Svanerudh |
| 7,454,244 B2 | 11/2008 | Kassab et al. |
| 7,458,938 B2 | 12/2008 | Patel et al. |
| 7,472,601 B1 | 1/2009 | Tenerz et al. |
| 7,481,774 B2 | 1/2009 | Brockway et al. |
| 7,527,594 B2 | 5/2009 | Vardi et al. |
| 7,532,920 B1 | 5/2009 | Ainsworth et al. |
| 7,599,588 B2 | 10/2009 | Eberle et al. |
| 7,645,233 B2 | 1/2010 | Tulkki et al. |
| 7,660,492 B2 | 2/2010 | Bates et al. |
| 7,724,148 B2 | 5/2010 | Samuelsson et al. |
| 7,731,664 B1 | 6/2010 | Millar |
| 7,775,988 B2 | 8/2010 | Pijls |
| 7,783,338 B2 | 8/2010 | Ainsworth et al. |
| 7,837,650 B1 | 11/2010 | Cox et al. |
| 7,881,573 B2 | 2/2011 | Eberle et al. |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,025,623 B1 | 9/2011 | Millar |
| 8,029,447 B2 | 10/2011 | Kanz et al. |
| 8,059,923 B2 | 11/2011 | Bates et al. |
| 8,140,146 B2 | 3/2012 | Kim et al. |
| 8,157,742 B2 | 4/2012 | Taylor |
| 8,162,856 B2 | 4/2012 | Williams et al. |
| 8,174,395 B2 | 5/2012 | Samuelsson |
| 8,187,195 B2 | 5/2012 | Tulkki |
| 8,216,151 B2 | 7/2012 | Smith |
| 8,231,537 B2 | 7/2012 | Ahmed et al. |
| 8,249,815 B2 | 8/2012 | Taylor |
| 8,277,386 B2 | 10/2012 | Ahmed et al. |
| 8,282,565 B2 | 10/2012 | Mahapatra et al. |
| 8,298,156 B2 | 10/2012 | Manstrom et al. |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson |
| 8,419,647 B2 | 4/2013 | Corl et al. |
| 8,419,648 B2 | 4/2013 | Corl et al. |
| 8,461,997 B2 | 6/2013 | Samuelsson |
| 8,485,985 B2 | 7/2013 | Manstrom |
| 8,556,520 B2 | 10/2013 | Elenbaas et al. |
| 8,562,537 B2 | 10/2013 | Alpert et al. |
| 8,636,659 B2 | 1/2014 | Alpert et al. |
| 8,641,639 B2 | 2/2014 | Manstrom |
| 8,696,584 B2 | 4/2014 | Kassab |
| 8,698,638 B2 | 4/2014 | Samuelsson et al. |
| 8,714,021 B2 | 5/2014 | Gamage |

(56) References Cited

U.S. PATENT DOCUMENTS

| | | |
|---|---|---|
| 8,797,155 B2 | 8/2014 | Huennekens et al. |
| 8,857,264 B2 | 10/2014 | Gamage |
| 8,860,851 B2 | 10/2014 | Goma et al. |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Corl et al. |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1 | 7/2004 | Armstrong et al. |
| 2004/0143261 A1 | 7/2004 | Hartley et al. |
| 2004/0157790 A1 | 8/2004 | Herweijer et al. |
| 2004/0162548 A1 | 8/2004 | Reiser |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan |
| 2005/0268724 A1 | 12/2005 | Tenerz |
| 2005/0268725 A1 | 12/2005 | Tulkki |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0142756 A1 | 6/2006 | Davies et al. |
| 2006/0207335 A1 | 9/2006 | Tenerz et al. |
| 2006/0241505 A1 | 10/2006 | Ahmed et al. |
| 2006/0287569 A1 | 12/2006 | Schock et al. |
| 2007/0060820 A1 | 3/2007 | Lofgren et al. |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1 | 6/2008 | Krishna |
| 2008/0200770 A1 | 8/2008 | Hubinette |
| 2008/0255471 A1 | 10/2008 | Maghavi et al. |
| 2008/0262470 A1 | 10/2008 | Lee et al. |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0248049 A1 | 10/2009 | Perkins |
| 2009/0281394 A1 | 11/2009 | Russell et al. |
| 2010/0014810 A1 | 1/2010 | Eberle et al. |
| 2010/0087732 A1 | 4/2010 | Eberle et al. |
| 2010/0109104 A1 | 5/2010 | Tiensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0234698 A1 | 9/2010 | Manstrom et al. |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0060229 A1 | 3/2011 | Hulvershorn |
| 2011/0066047 A1 | 3/2011 | Belleville et al. |
| 2011/0071407 A1 | 3/2011 | Hubinette et al. |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1 | 7/2012 | Smith |
| 2012/0172732 A1 | 7/2012 | Meyer |
| 2012/0203118 A1 | 8/2012 | Samuelsson et al. |
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0271178 A1 | 10/2012 | Smith |
| 2012/0278008 A1 | 11/2012 | Davies et al. |
| 2012/0316419 A1 | 12/2012 | Chevalier |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |
| 2013/0131523 A1 | 5/2013 | Suchecki et al. |
| 2013/0190633 A1 | 7/2013 | Dorando et al. |
| 2013/0216481 A1 | 8/2013 | Rosenmeier |
| 2013/0303914 A1 | 11/2013 | Hiltner et al. |
| 2013/0324864 A1 | 12/2013 | Manstrom et al. |
| 2014/0024235 A1 | 1/2014 | Russell |
| 2014/0024950 A1 | 1/2014 | Hiltner et al. |
| 2014/0086461 A1 | 3/2014 | Yao et al. |
| 2014/0180140 A1 | 6/2014 | Alpert |
| 2014/0180141 A1* | 6/2014 | Millett ............... A61B 5/0215 600/486 |
| 2014/0187980 A1 | 7/2014 | Burkett |
| 2014/0187984 A1 | 7/2014 | Burkett |
| 2014/0276142 A1 | 9/2014 | Dorando |

(56) References Cited

U.S. PATENT DOCUMENTS

| | | |
|---|---|---|
| 2014/0379269 A1 | 12/2014 | Schmitt |
| 2015/0032011 A1 | 1/2015 | McGowan et al. |
| 2015/0074995 A1* | 3/2015 | Patil .................. A61B 5/02007 29/855 |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0223707 A1 | 8/2015 | Ludoph |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1 | 12/2015 | McCaffrey et al. |
| 2015/0359439 A1 | 12/2015 | Manstrom et al. |
| 2016/0022153 A1 | 1/2016 | Dorando |
| 2016/0066802 A1 | 3/2016 | Keller |
| 2016/0106321 A1 | 4/2016 | Sharma et al. |

FOREIGN PATENT DOCUMENTS

| | | |
|---|---|---|
| EP | 1260175 | 11/2002 |
| EP | 1493381 | 1/2005 |
| EP | 1 165 171 | 3/2005 |
| EP | 1514512 | 3/2005 |
| EP | 1658808 | 5/2006 |
| EP | 1702641 | 9/2006 |
| EP | 1 498 068 | 3/2007 |
| EP | 01419796 B1 | 3/2008 |
| JP | 10033488 | 2/1998 |
| JP | 10137199 | 5/1998 |
| JP | 2000-333913 | 12/2000 |
| JP | 2005-3638066 | 1/2005 |
| JP | 2005-095603 | 4/2005 |
| JP | 2005-3705458 | 8/2005 |
| JP | 2006-204378 | 8/2006 |
| NL | 2009285 | 2/2014 |
| WO | WO97/00641 | 1/1997 |
| WO | WO1999/058059 | 11/1999 |
| WO | WO2003/022122 | 3/2003 |
| WO | WO2006/037082 | 4/2006 |
| WO | WO2006/0117154 | 11/2006 |
| WO | WO2011/120565 | 10/2011 |
| WO | WO2011/0161212 | 12/2011 |
| WO | WO2012093260 | 7/2012 |
| WO | WO2012173697 | 12/2012 |
| WO | WO2013061281 | 5/2013 |
| WO | WO2014/025255 | 2/2014 |
| WO | WO2014/176448 | 10/2014 |
| WO | WO2015/150128 | 10/2015 |
| WO | WO2016/001017 | 1/2016 |

OTHER PUBLICATIONS

PCT/US2017/022637, The International Search Report and the Written Opinion of the International Searching Authority, dated Jul. 12, 2017, 12 pages.

Restriction Requirement dated Jul. 27, 2018 in co-pending U.S. Appl. No. 15/077,964.

Final Office Action in co-pending U.S. Appl. No. 14/920,722, dated Sep. 27, 2018.

International Preliminary Report on Patentability in PCT/US2017/022637, dated Oct. 4, 2018.

* cited by examiner

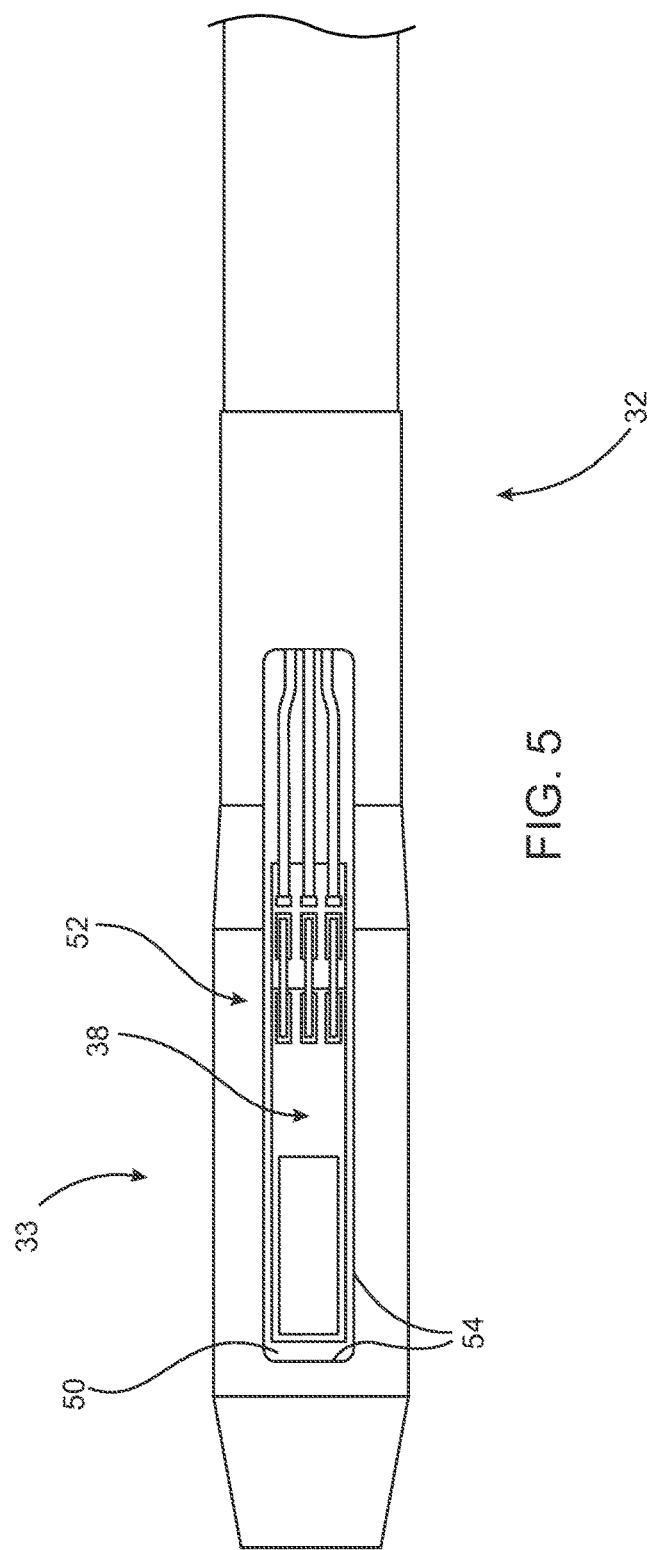

FIG. 6

PRESSURE MEASURING CATHETER HAVING REDUCED ERROR FROM BENDING STRESSES

RELATED APPLICATIONS

The present application claims the benefit under 35 U.S.C. § 119 of U.S. Provisional Patent Application No. 62/012,628 filed on Jun. 16, 2014 and titled FFR MICRO-CATHETER RIGID TIP AND CANTILEVER DESIGN.

FIELD OF THE INVENTION

The invention relates to methods and systems for determining a pressure gradient across a lesion of a vessel for calculating a Fractional Flow Reserve.

BACKGROUND OF THE INVENTION

The severity of a stenosis or lesion in a blood vessel may be assessed by obtaining proximal and distal pressure measurements relative to the given stenosis and using those measurements for calculating a value of the Fractional Flow Reserve (FFR). FFR is defined as the ratio of a first pressure measurement ($P_d$) taken on the distal side of the lesion and to a second pressure measurement taken on the proximal side of the lesion usually within the aorta ($P_a$). Conventionally, a sensor is placed on the distal portion of a guidewire or FFR wire to obtain the first pressure measurement $P_d$, while an external pressure transducer is fluidly connected via tubing to a guide catheter for obtaining the second or aortic (AO) pressure measurement $P_a$. Calculation of the FFR value provides a lesion specific index of the functional severity of the stenosis in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation.

If an interventional treatment is required, the interventional device, such as a balloon catheter, is tracked over a guide wire to the site of the lesion. Conventional FFR wires generally are not desired by clinicians to be used as guide wires for such interventional devices. Accordingly, if an intervention treatment is required, the clinician generally removes the FFR wire, inserts a conventional guide wire, and tracks the interventional device to the treatment site over the conventional guide wire.

The mounting of a pressure sensor on the distal end of a catheter, such as a microcatheter makes it difficult to isolate the pressure sensor from bending stresses experienced as a result of interaction between the pressure sensor and the housing of the catheter. Due to the high sensitivity and size of the pressure sensor used in this application, any stress placed on the pressure sensor can cause a distortion of the sensor resulting in an incorrect pressure reading or bend error. Accordingly, there remains a need for a microcatheter to obtain pressure measurements suitable for use in calculating an FFR value for a given stenosis, whereby the clinician may use a conventional or preferential guidewire instead of a FFR guidewire. In addition, there remains a need for a FFR microcatheter to reduce the amount of bending stresses experienced by the pressure sensor in order to minimize bending error in the pressure reading.

BRIEF SUMMARY OF THE INVENTION

Embodiments hereof relate to a catheter, such as a pressure measurement catheter, including an elongate shaft having a proximal end optionally coupled to a handle or luer fitting and a distal end having a distal opening. The elongate shaft further includes a proximal portion, an intermediate portion, and a distal portion having a distal tip. In the proximal portion of the elongated shaft, a shaft wall may define two separate lumens: a guide wire lumen and a second or pressure sensor wire lumen, extending parallel to each other or side-by-side along the proximal portion. The distal portion of the elongate shaft is configured to receive a guidewire in a distal portion of guidewire lumen thereof. The pressure sensing wire lumen may extend to the distal portion of the elongate shaft to be coupled to a pressure sensor disposed in a pocket of the distal tip for measuring a pressure of a fluid within lumen of vessel. Pressure sensor may be mounted on top of an interposer such that the sensor is elevated above the shaft wall and spaced apart from the sidewalls of the pocket, thereby isolating the pressure sensor from the bending stresses of the catheter.

Embodiments hereof also relate to a catheter, such as a measurement catheter, including an elongate shaft having a proximal end optionally coupled to a handle or luer fitting and a distal end having a distal opening. The elongate shaft further includes a proximal portion, an intermediate portion, and a distal portion having a distal tip. In the proximal portion of elongated shaft, shaft wall may define two separate lumens: a guide wire lumen and a second or pressure sensor wire lumen, extending parallel to each other or side-by-side along the proximal portion. The distal portion of the elongate shaft is configured to receive a guidewire in a distal portion of the guidewire lumen thereof. The pressure sensing wire lumen may extend to the distal portion of the elongate shaft to be coupled to a pressure sensor disposed in a pocket of the distal tip for measuring a pressure of a fluid within lumen of vessel. A step can be formed into the shaft wall under the pressure sensor such that the pressure sensor is elevated above the shaft wall and spaced apart from the sidewalls of the pocket, thereby isolating the pressure sensor from the bending stresses applied to the catheter.

Embodiments hereof also relate to a catheter, such as a measurement catheter, including an elongate shaft having a proximal end optionally coupled to a handle or luer fitting and a distal end having a distal opening. The elongate shaft further includes a proximal portion, an intermediate portion, and a distal portion having a distal tip. In the proximal portion of elongated shaft, shaft wall may define two separate lumens: a guide wire lumen and a second or pressure sensor wire lumen, extending parallel to each other or side-by-side along the proximal portion. The distal portion of the elongate shaft is configured to receive a guidewire in a distal portion of the guidewire lumen thereof. The pressure sensing wire lumen may extend to the distal portion of the elongate shaft to be coupled to a pressure sensor disposed in a pocket of the distal tip for measuring a pressure of a fluid within lumen of vessel. The pressure sensor may have an elongate portion and a support portion, whereby the support portion elevates the pressure sensor above the shaft wall and the pressure sensor is spaced apart from the sidewalls of the pocket in order to isolate the pressure sensor from the bending stresses applied to the catheter.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 5 is a detailed top view of the distal portion of the catheter of FIG. 4 including a pocket and the pressure sensor.

FIG. 6 is a perspective view of the catheter of FIG. 4 with elements of the catheter removed to show a more detailed view of the pressure sensor and shaft wall.

DETAILED DESCRIPTION OF THE INVENTION

Specific embodiments of the present invention are now described with reference to the figures, wherein like reference numbers indicate identical or functionally similar elements. While the disclosure refers to illustrative embodiments for particular applications, it should be understood that the disclosure is not limited thereto. Modifications can be made to the embodiments described herein without departing from the scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" and "distally" are positions distant from or in a direction away from the clinician. "Proximal" and "proximally" are positions near or in a direction toward the clinician.

Figure 1:
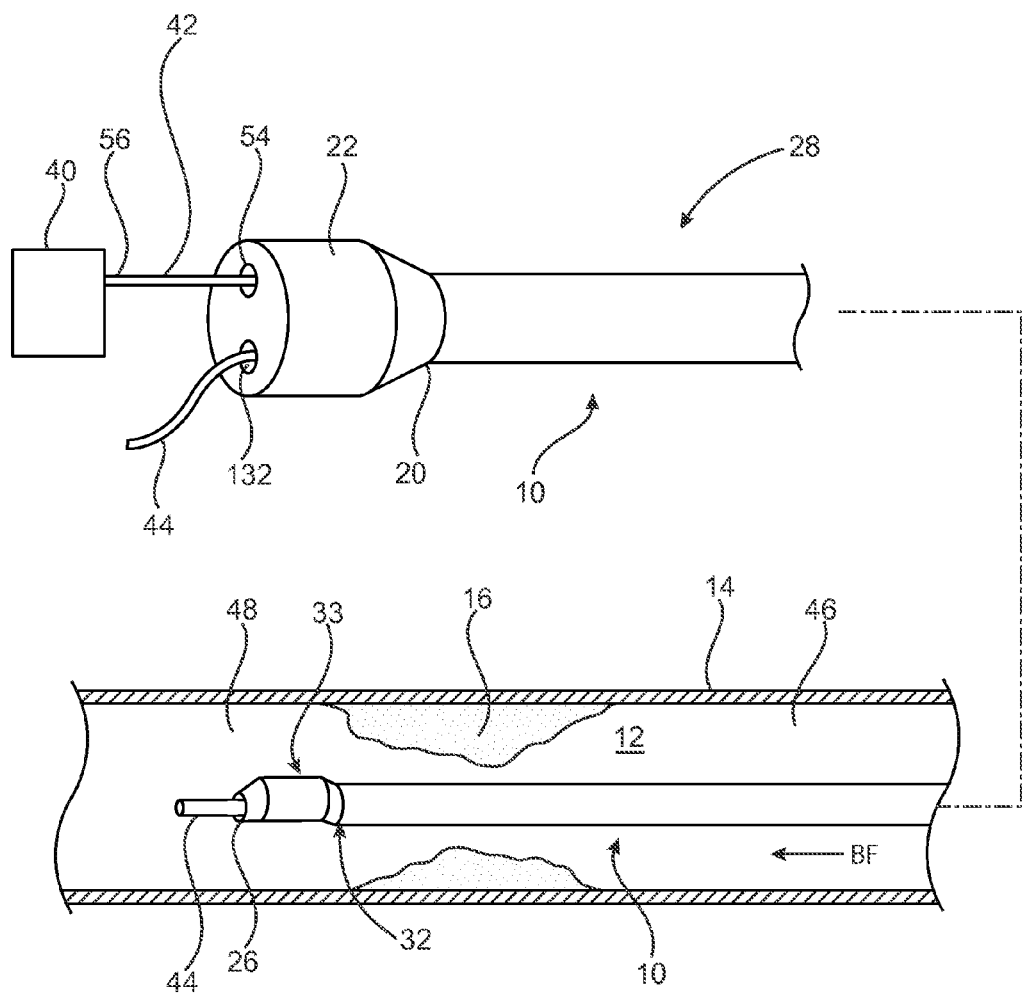
FIG. 1 is a broken view of a system for measuring FFR with a distal portion thereof shown within a vessel including a lesion, the system including a measurement catheter including a pressure sensor and a guidewire, in accordance with an embodiment hereof.

With reference to FIG. 1, a pressure measurement catheter 10 is shown with a proximal portion thereof outside of a patient and a distal portion thereof positioned in situ within a lumen 12 of a patient vessel 14 having a stenosis or lesion 16. In an embodiment hereof, the vessel 14 is a blood vessel such as but not limited to a coronary artery. Lesion 16 is generally representative of any blockage or other structural arrangement that results in a restriction to the flow of fluid through lumen 12 of vessel 14. Lesion 16 may be a result of plaque buildup, including without limitation plaque components such as fibrous, fibro-lipidic (fibro fatty), necrotic core, calcified (dense calcium), blood, fresh thrombus, and mature thrombus. Generally, the composition of lesion will depend on the type of vessel being evaluated. In that regard, it is understood that embodiments hereof are applicable to various types of blockage or other narrowing of a vessel that results in decreased fluid flow.

Figure 2:
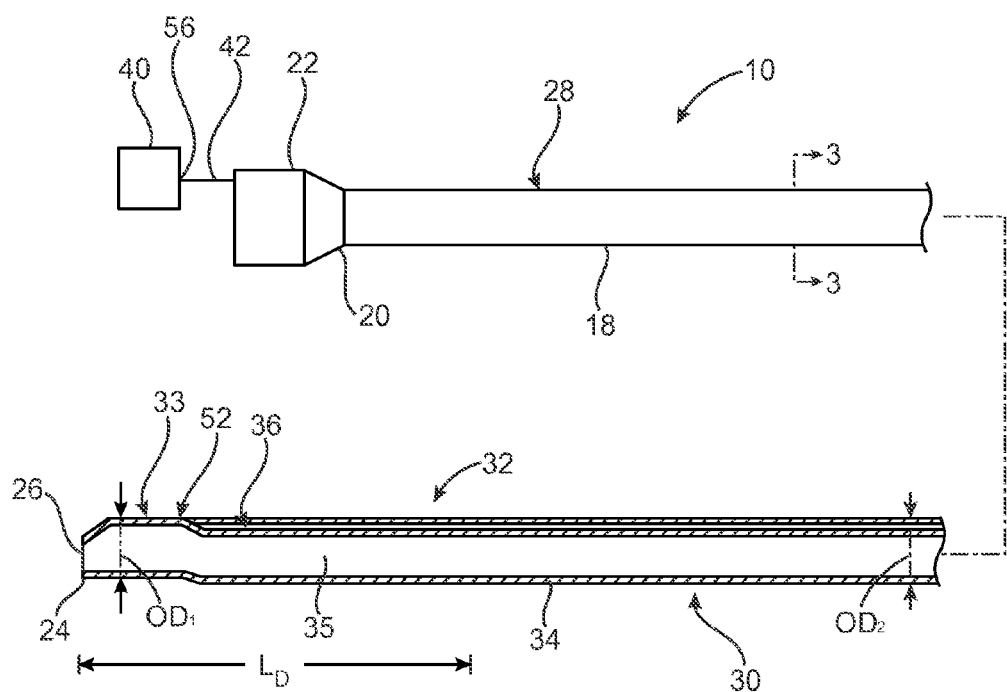
FIG. 2 is a broken view of the catheter of FIG. 1 in partial longitudinal cross-section.

Measurement catheter 10 is shown in FIG. 2 with a distal portion thereof in longitudinal cross-section. Measurement catheter 10 includes an elongate shaft 18 having a proximal end 20 that may be coupled to a handle or luer fitting 22 and a distal end 24 having a distal opening 26. Elongate shaft 18 further includes a proximal portion 28, an intermediate portion 30, and a distal portion 32 having a distal tip 33. Although proximal portion 28, intermediate portion 30, and distal portion 32 of elongate shaft 18 have been described separately, they are described in such a manner for convenience and elongate shaft 18 may be constructed unitarily such that the portions described are part of a unitary shaft. However, different portions of elongate shaft 18 may also be constructed separately and joined together.

In embodiments hereof, elongate shaft 18 or component and/or segments thereof may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. Optionally, the catheter shaft or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like. In one embodiment, for example, at least a proximal portion of elongate shaft 18 may be formed from a reinforced polymeric tube. In other embodiments of an elongate tubular shaft or component in accordance herewith, a proximal segment thereof may be a hypotube of a medical grade stainless steel with outer and inner tubes of a distal segment thereof being formed from any of the polymeric materials listed above.

Figure 3:
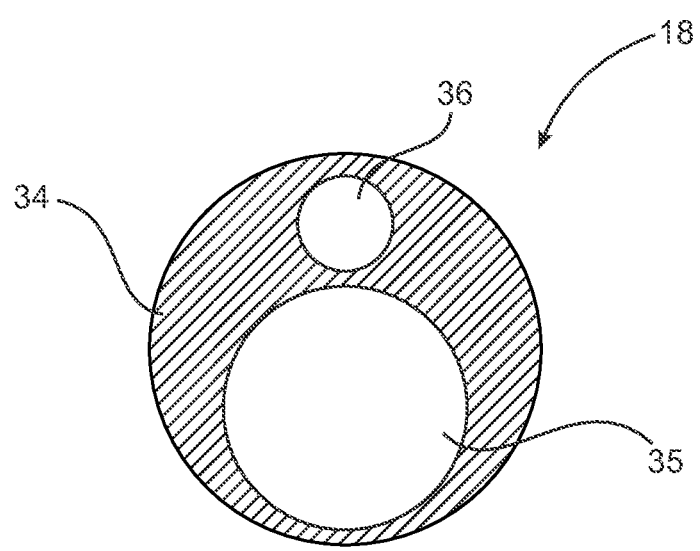
FIG. 3 is a cross-sectional view of the catheter taken along line 3-3 of FIG. 2.
Figure 4:
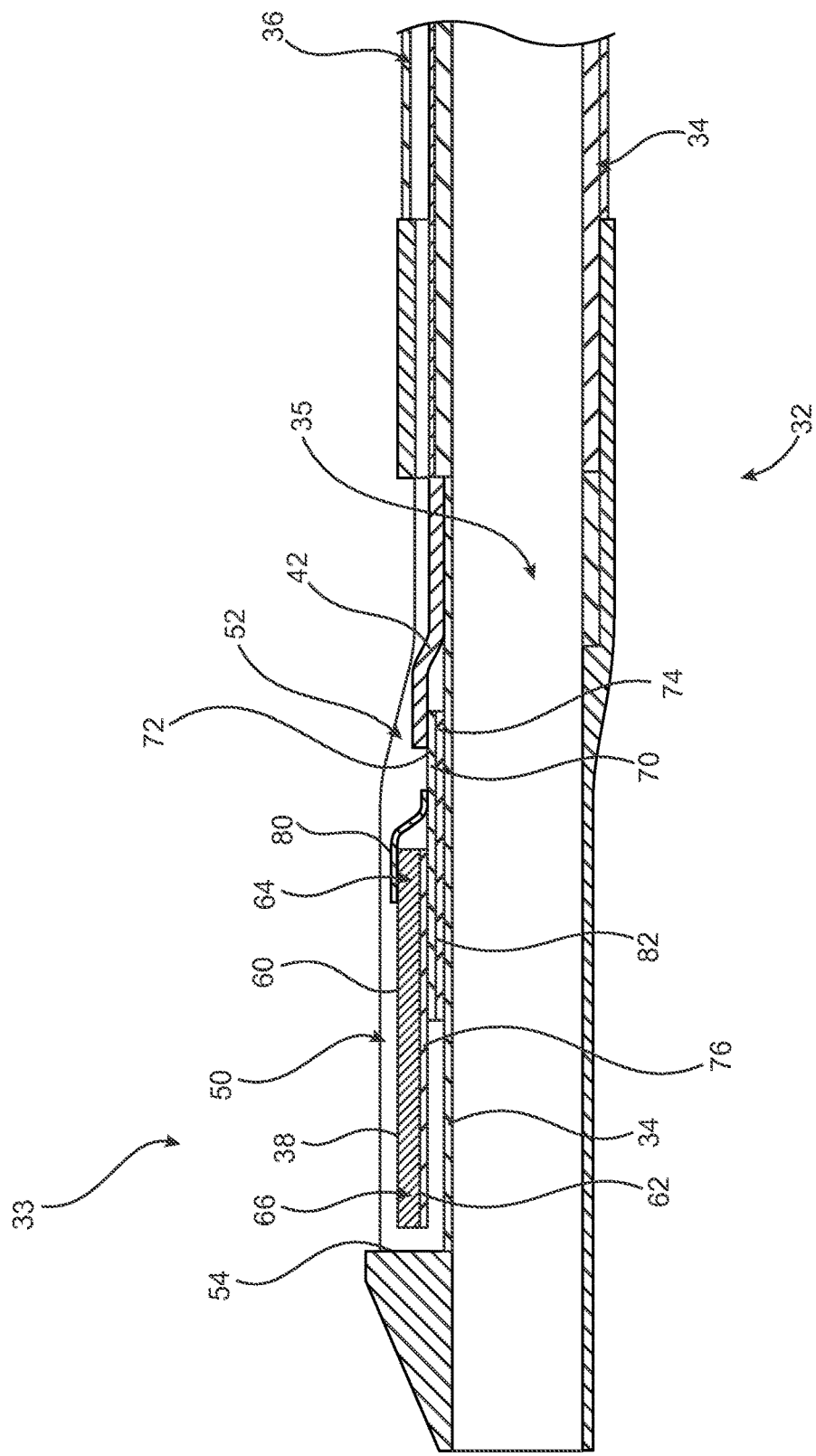
FIG. 4 is an illustration of the distal portion of the catheter of FIG. 1 in longitudinal cross-section.

As shown in FIGS. 2-3, elongate shaft 18 has a shaft wall 34 defining a guide wire lumen 35 extending therethrough. Guide wire lumen 35 extends through proximal portion 28, intermediate portion 30, and distal portion 32. However, instead of the over-the-wire configuration shown in FIGS. 1-3, catheter 10 may have a rapid exchange configuration wherein guide wire lumen 35 extends through distal portion 32 and intermediate portion 30, and the guidewire exits shaft 18 through a rapid exchange port (not shown) in proximal portion 28, as would be understood by those skilled in the art. In one embodiment, with reference to the cross-sectional view of FIG. 3 (taken along line 3-3 of FIG. 2), in proximal portion 28 of elongated shaft 18, shaft wall 34 defines two separate lumens, guide wire lumen 35 and a second or pressure sensor wire lumen 36, extending parallel to each other or side-by-side along proximal portion 28. Communication wires 42 are omitted in FIG. 3 for clarity. Although depicted as circular in cross-section, one or more lumen(s) of elongated shaft 18 may have any suitable cross-section including for example circular, elliptical, rectangular or crescent-shaped. As explained in more detail below, pressure sensing wire lumen 36 may extend to distal portion 32 of elongate shaft 18 to be coupled to a pressure sensor 38, as shown in FIGS. 4-5. In one embodiment, pressure sensor wire lumen 36 may be eliminated wherein a signal from pressure sensor 38 is sent to a computing device 40 other than via a wire 42 in a dedicated pressure sensor wire lumen 36, such as, but not limited to, wireless transmission or integration of wire 42 into the wall of elongate shaft 18. In other embodiments of an elongate shaft or tubular component in accordance herewith, pressure sensor wire lumen 36 may be eliminated wherein the shaft or a portion thereof may be formed by a tubular polymeric inner liner overlaid with a power lead layer and a polymeric outer jacket. In such an embodiment, the power leads for the respective pressure sensor of the inner shaft may be wrapped around the respective shaft for all or at least a portion of the shaft and secured in position by the polymeric outer jacket so as to be embedded within the shaft. In another such embodiment, the power lead for the respective pressure sensor of the inner shaft may be straight for a section or for the entire length of the shaft, and secured in position against the inner liner by the polymeric outer jacket so as to be embedded within the shaft.

Distal portion 32 of elongate shaft 18 is configured to receive a guidewire 44 in a distal portion of guidewire lumen 35 thereof. Further, as shown in FIG. 1, distal portion 32 is sized to extend from a proximal side 46 of lesion 16, through lesion 16, and to a distal side 48 of lesion 16 such that distal tip 33 is disposed on distal side 48 of lesion 16. Accordingly, in an embodiment, distal portion 32 has a length $L_D$ in the range of 25-300 mm. However, length $L_D$ may be any length suitable such that distal portion 32 may extend from proximal side 46 to distal side 48. Further, because distal portion 32 is configured to extend through lesion 16, the cross-sectional dimension or profile of distal portion 32 is minimized such as to minimize the disruption of blood flow through lesion 16 in order to obtain an accurate FFR measurement.

Distal tip 33 is disposed on distal portion 32 of elongate shaft 18. In an optional embodiment (not shown), distal tip 33 is disposed on intermediate portion 30 of elongate shaft 18 and is located proximally of distal portion 32. Distal tip 33 includes pressure sensor 38 for measuring a pressure of a fluid within lumen 12 of vessel 14, as shown in FIGS. 4-5. In the embodiment shown in FIGS. 4-5, pressure sensor 38 is disposed in a pocket 50 of a thickened portion 52 of distal tip 33. As shown in FIGS. 4-5, pocket 50 may be defined by at least one substantially vertical sidewall 54 and substantially horizontal shaft wall 34. In another embodiment, pocket 50 has at least one sidewall with a curvilinear shape. Pressure sensor 38 may be a piezo-resistive pressure sensor, a piezo-electric pressure sensor, a capacitive pressure sensor, an electromagnetic pressure sensor, an optical pressure sensor, and/or combinations thereof. In one non-limiting example pressure sensor 38 is a micro electromechanical sensor (MEMS) based pressure die measuring about 240 microns by 70 microns by 1100 microns in size. However, other sized pressure sensors may be used. As shown in FIG. 2, thickened portion 52 needs to accommodate pressure sensor 38. Accordingly, thickened portion 52 of elongate shaft 18 causes tip portion 33 to have an outer diameter $OD_1$ (shown in FIG. 2) which is larger than the outer diameter $OD_2$ of distal portion 32 of elongate shaft 18. However, depending on the size of pressure sensor 38, the outer diameters $OD_1$ and $OD_2$ of the elongate shaft 18 could have substantially the same diameter. In one embodiment, outer diameter $OD_1$ of tip portion 33 is in the range of 0.024 inch-0.040 inch in order to accommodate pressure sensor 38. However, outer diameter $OD_1$ may vary depending on the size of pressure sensor 38, thickness of elongate shaft 18, and other factors used to determine the diameter or profile of shafts. In an optional embodiment, a cover (not shown) could extend substantially over pocket 50 to protect pressure sensor 38 from contacting the vessel wall while still allowing blood flow to surround pressure sensor 38.

Pocket 50 is in communication with pressure sensor wire lumen 36 such that any communication wire(s) 42 from pressure sensor 38 may extend from pocket 50 proximally through pressure sensor wire lumen 36, through a corresponding lumen in luer fitting 22 exiting through proximal port 54 to a computing device 40 coupled to proximal end 56 of communication wire 42. Proximal end 56 of communication wire 42 may be coupled to computing device 40 via various communication pathways, including but not limited to one or more physical connections including electrical, optical, and/or fluid connections, a wireless connection, and/or combinations thereof. Accordingly, it is understood that additional components (e.g., cables, connectors, antennas, routers, switches, etc.) not illustrated in FIG. 1 may be included to facilitate communication between the proximal end 56 of communication wire 42 and computing device 40. In an optional embodiment, computing device 40 is incorporated into catheter 10 or for example, in proximal portion 28.

FIG. 4 is a cross-sectional view of distal tip 33. Therein, sensor 38 has a first surface 60, second surface 62, first end 64 and a second end 66. Communication wires 42 (for example, 0.0025 inch coated copper wire in a tri-filar configuration) extending from lumen 36 are coupled to an electrical interface, such as an interposer 70 which has first and second surfaces 72, 74. In this embodiment, communication wires 42 form an "S-shape", such that one end of the communication wires 42 is raised up to the elevated level of first surface 72 of interposer 70. Second sensor surface 62 is coupled to first surface 72 of interposer 70 (for example, by an adhesive 76), thereby disposing interposer between shaft wall 34 of elongate shaft 18 and sensor 38. FIG. 5 is a top view of distal tip 33 showing pocket 50 open to the environment. Thus, sensor 38, wires 42, 80 and interposer 70 are in communication with a fluid within lumen 12 of vessel 14.

Figure 4A:
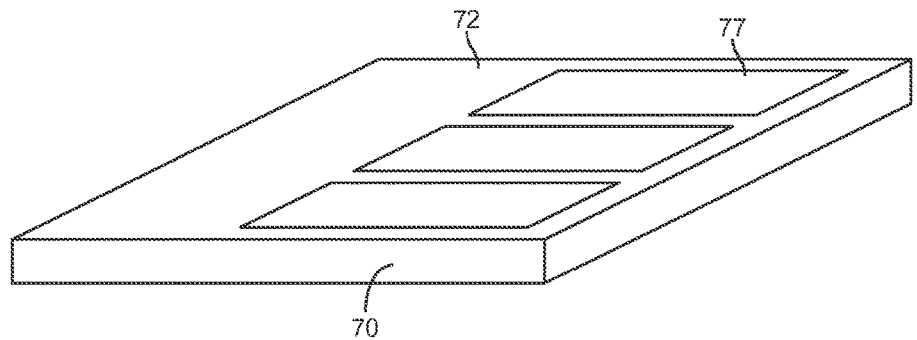
FIG. 4A is a perspective view of an interposer with electrical contact pads.
Figure 4B:
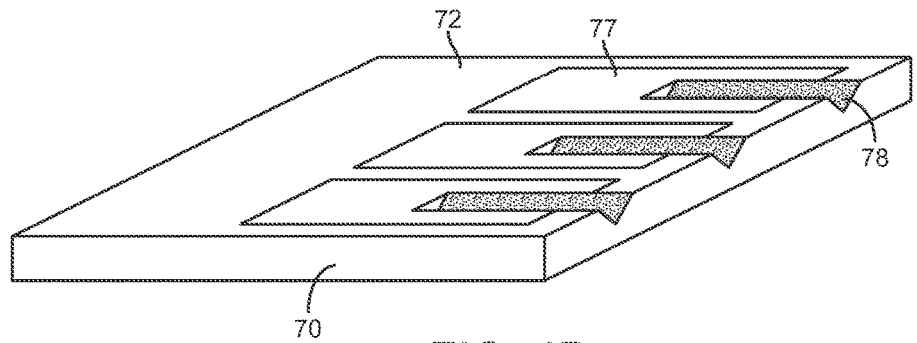
FIG. 4B is a perspective view of another embodiment of an interposer with grooves formed in the electrical contact pads.
Figure 4C:
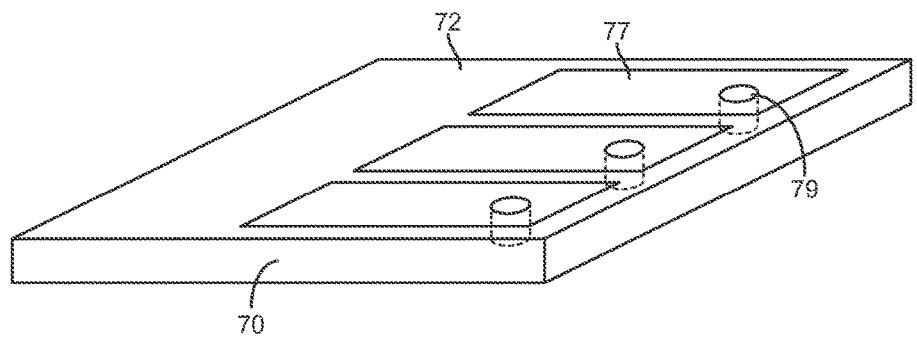
FIG. 4C is a perspective view of another embodiment of an interposer with holes formed in the electrical contact pads.

Sensor wires 80 (for example, 0.001 inch gold wires) have a first end coupled to first surface 72 of interposer 70 and a second end coupled to first surface 60 of sensor 38. Similarly to the communication wires, sensor wires may also make an S-shape, such that one end of the sensor wires 80 is raised up to the elevated level of first surface 60 of sensor 38. Because electrical contact pads 77 (as shown in FIG. 4A) on sensor 38 are extremely small (for example 0.200 mm length×0.050 mm width) and the metallization profile is dependent on the manufacturer, the use of an interposer optimizes the size, layout and metallization of the pads. In another embodiment shown in FIG. 4B, grooves 78 are formed into interposer 70 to better facilitate the coupling (for example by welding or soldering) of communication wires 42 or sensor wires 80 to interposer 70. Grooves 78 form a V-shaped cross section (however other cross sectional shapes are possible) and extend from the one end of interposer 70 into electrical contact pads 77. Since interposer 70 and communication and sensor wires 42, 80 are relatively small, grooves 78 help guide communication and sensor wires 42, 80 into proper placement onto first surface 72 of interposer 70. In another embodiment shown in FIG. 4C, holes 79 are formed into contact pads 77 to better facilitate the placement and coupling (for example by welding or soldering) of communication wires 42 or sensor wires 80 to interposer 70. Holes 79 are cylindrical in shape (however, other shapes are possible) and extend through electrical contacts pads 77 and into interposer 70.

Figure 6:
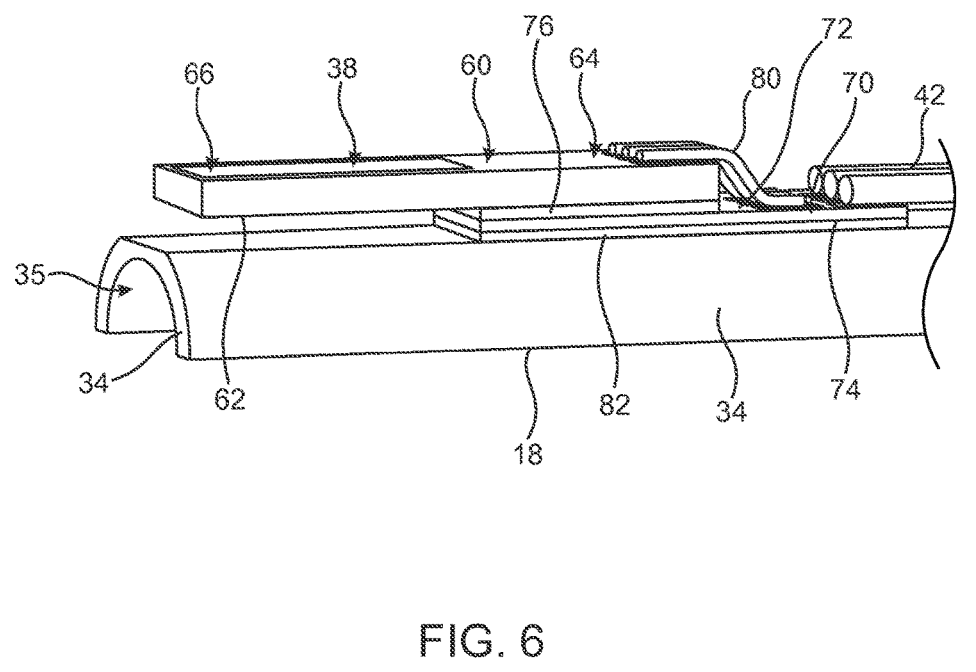

FIG. 6 is an enlarged perspective view of sensor 38, wires 42, 80 and interposer 70. Other portions of catheter 10 are removed to better show specific attributes of the present Invention. Interposer 70 has second surface 74 coupled to shaft wall 34 of elongate shaft 18. In one embodiment, interposer 70 is coupled to shaft wall 34 by an adhesive 82 having a layer depth of about 25 microns. As described above, bending stresses experienced when tracking a microcatheter through the vasculature may create a distortion of the sensor resulting in an incorrect pressure reading or bend error. In order to isolate sensor 38 from bending stresses, sensor 38 may be mounted with first end 64 of sensor 38 coupled to first surface 72 of interposer 70 while second end 66 of sensor 38 may be suspended above shaft wall 34. Thus, second end 66 of sensor 38 may not be coupled to any portion of catheter 10. Hence, sensor 38 may be cantilever mounted with proximal portion of sensor 38 coupled to interposer 70. Second surface 62 of sensor 38 may be spaced apart from shaft wall 34 by having a void disposed between second surface 62 of sensor 38 and shaft wall 34. Sensor 38 may be elevated above shaft wall 34 by the thickness of interposer 70 and to some degree by the thickness of the adhesive layers 76 and 82. Sensor 38 may be elevated above shaft wall 34 by a distance of about 40-50 microns. In an optional embodiment, the amount of distance between the sensor 38 and shaft wall 34 is about 25-60 microns.

Second end 66 of sensor 38 may be spaced apart from sidewall 54 of pocket 50 by having a void disposed between sensor 38 and sidewall 54 of pocket 50. Put another way, distal portion of sensor 38 may be free floating with respect to catheter shaft 18. Thus, as shown in FIG. 6, sensor 38 can be exposed to the environment and first surface 60, second surface 62 and second end 66 would be surrounded by a fluid when catheter 10 is disposed within lumen 12 of vessel 14. In one embodiment, at least a portion of sensor 38 is suspended above shaft wall 34. In another embodiment, about half of sensor 38 is suspended above shaft wall 34. In yet another embodiment, more than half of sensor 38 is suspended above shaft wall 34. Thus, any length of sensor 38 can be suspended above shaft wall 34 depending on where first end 64 of sensor 38 is mounted onto interposer 70.

Figure 7A:
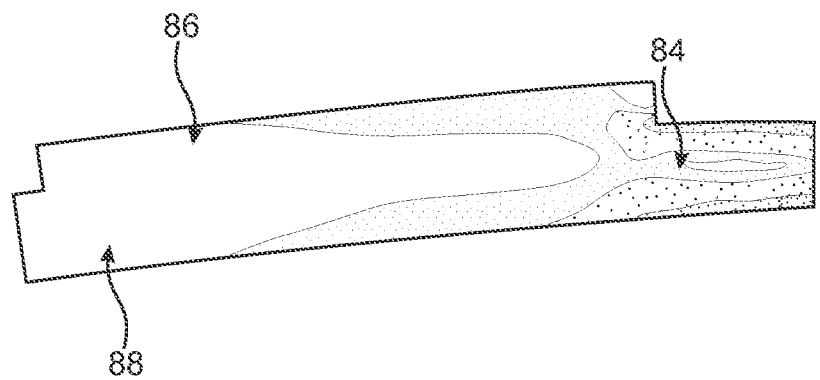
FIG. 7A is a finite element analysis representation of a sensor mounted on an elongate body showing bending induced stresses on the sensor membrane.
Figure 7B:
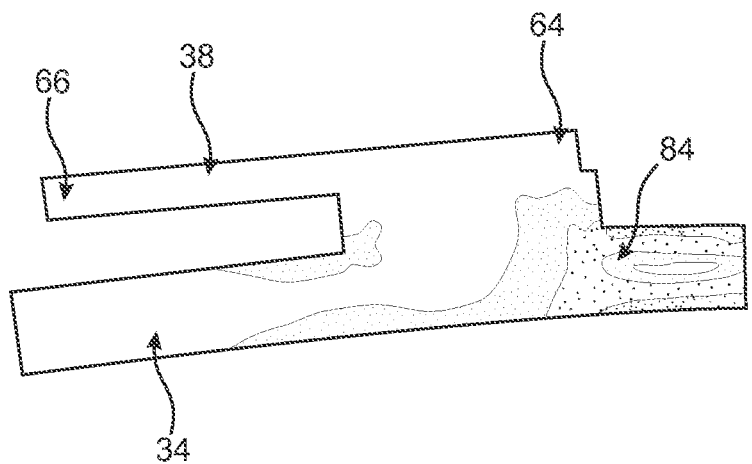
FIG. 7B is a finite element analysis representation of a sensor suspended above an elongate body showing isolation of sensor membrane from bending induced stresses.

By suspending at least a portion of sensor 38 above shaft wall 34, sensor 38 may be isolated from shaft wall 34 and further isolated from elongate body 18 which is experiencing the bending stresses. Put another way, if the entire length of sensor 38 were coupled to shaft wall 34 of elongate body 18, then sensor 38 could experience substantially the same bending stresses as shaft wall 34 of elongate body 18. FIG. 7a shows finite element analysis (FEA) results of Von Mises stresses 84 present in a sensor 86 directly mounted to a shaft wall 88 of an elongate body of a catheter. As compared to sensor 38 with a second end 66 suspended above shaft wall 34 of elongate body 18 as shown in FIG. 7b. The Von Mises stresses 84 shown in FIGS. 7a and 7b graphically show varying stress intensities experienced by each embodiment. As can be seen in FIG. 7a, bending stresses extend from the shaft wall 88 of the elongate body into the sensor 86. Whereas in FIG. 7b, the bending stresses are isolated to just shaft wall 34, and the bending stresses do not extend into sensor 38. By isolating the sensor 38 from bending stresses, the integrity of sensor 38 can remain intact and the accuracy of the measurements of sensor 38 can be improved.

Figure 8:
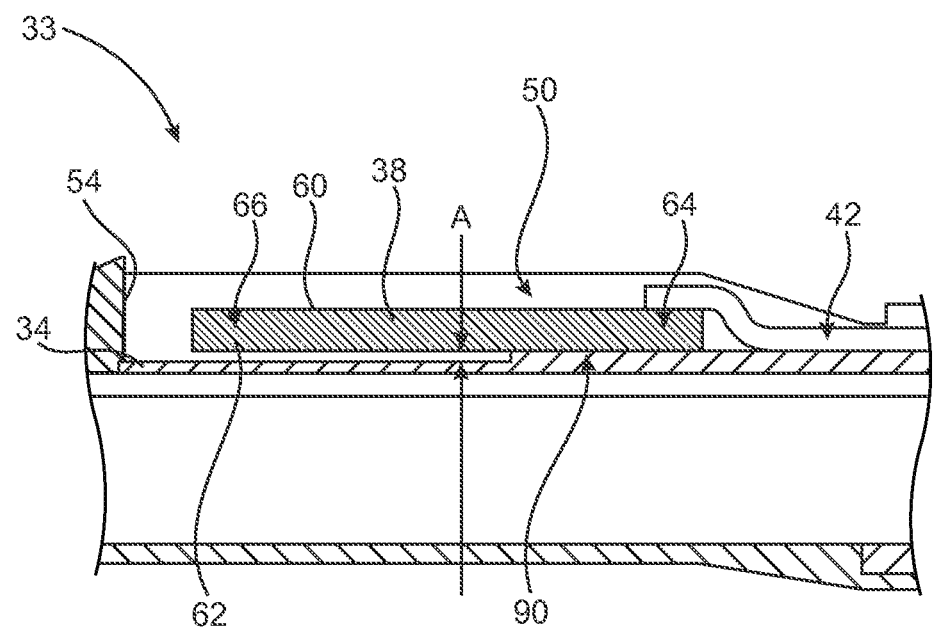
FIG. 8 illustrates a distal portion of an embodiment of the catheter of FIG. 1 in longitudinal cross-section.

FIG. 8 is an enlarged cross-sectional view of another embodiment of distal tip 33. In the embodiment of FIG. 8, distal tip 33 does not have an interposer or sensor wires. Instead, communication wires 42 are coupled directly to first surface 60 of sensor 38. Sensor 38 has second surface 62 coupled to shaft wall 34 of elongate body 18, such as by an adhesive. In order to suspend sensor 38 above shaft wall 34, a step 90 is formed or etched into shaft wall 34 to create a void between second surface 62 of sensor 38 and shaft wall 34. In one embodiment, distance A, which is the measurement of step 90, measures about 40 to 50 microns or in another embodiment about 25 to 50 microns. As previously described with reference to FIG. 6, second end 66 of sensor 38 may also be spaced apart from sidewall 54 of pocket 50 by having a void disposed between sensor 38 and sidewall 54 of pocket 50. With second end 66 spaced apart from shaft wall 34 and sidewalls 54, at least a portion of sensor 38 may be exposed to the environment and first and second surfaces 60, 62 could be surrounded by a fluid when catheter 10 is disposed within lumen 12 of vessel 14.

Figure 9:
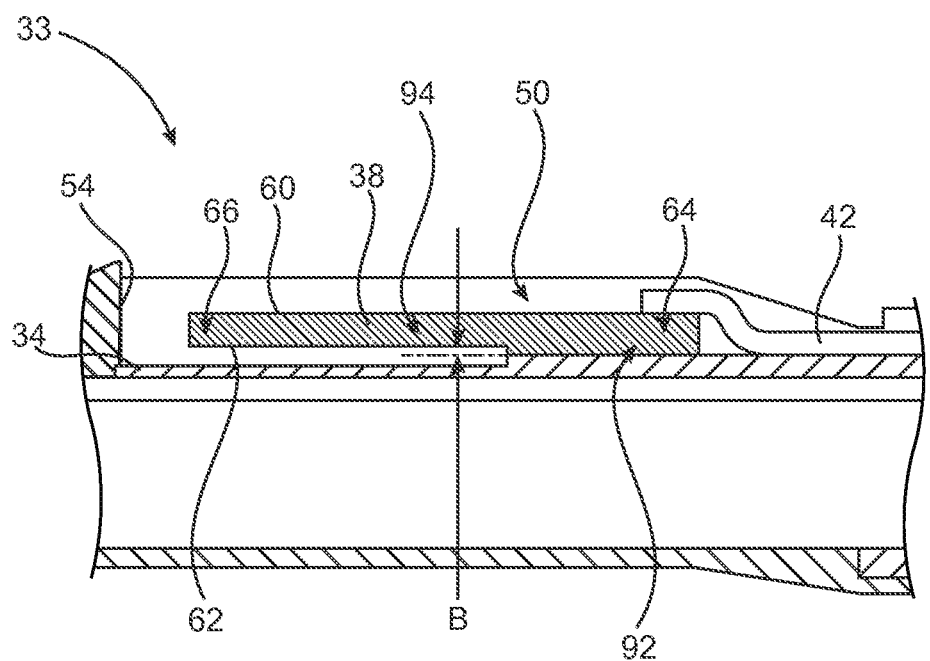
FIG. 9 illustrates a distal portion of another embodiment of the catheter of FIG. 1 in longitudinal cross-section.

FIG. 9 is an enlarged cross-sectional view of another embodiment of distal tip 33. In the embodiment of FIG. 9, distal tip 33 does not have an interposer, sensor wires or a step formed into shaft wall 34. Instead, sensor 38 has a support portion 92 adjacent first end 64, and an elongate portion 94. Thus, support portion 92 and elongate portion 94 when taken together may form a unitary or one-piece sensor 38. Communication wires 42 are directly coupled to first surface 60 of sensor 38. Support portion 92 of sensor 38 is coupled to shaft wall 34 by, for example, an adhesive. Support portion 92 elevates elongate portion 94 above shaft wall 34 creating a void between second surface 62 of sensor 38 and shaft wall 34. In the embodiment shown in FIG. 9, distance B, which is the thickness of support portion 92, measures about 20 to 25 microns or in another embodiment, about 10 to 30 microns. Thus, second surface 62 of elongate portion 94 of sensor 38 is spaced apart from shaft wall 34 by having a void disposed between second surface 62 of sensor 38 and shaft wall 34. As previously described with reference to FIG. 6, second end 66 of sensor 38 may be spaced apart from sidewall 54 of pocket 50 by having a void disposed between sensor 38 and sidewall 54 of pocket 50. With second end 66 spaced apart from shaft wall 34 and sidewall 54, at least a portion of sensor 38 may be exposed to the environment and first surface 60, second surface 62 and second end 66 could be surrounded by a fluid when catheter 10 is disposed within lumen 12 of vessel 14.

Figure 10:
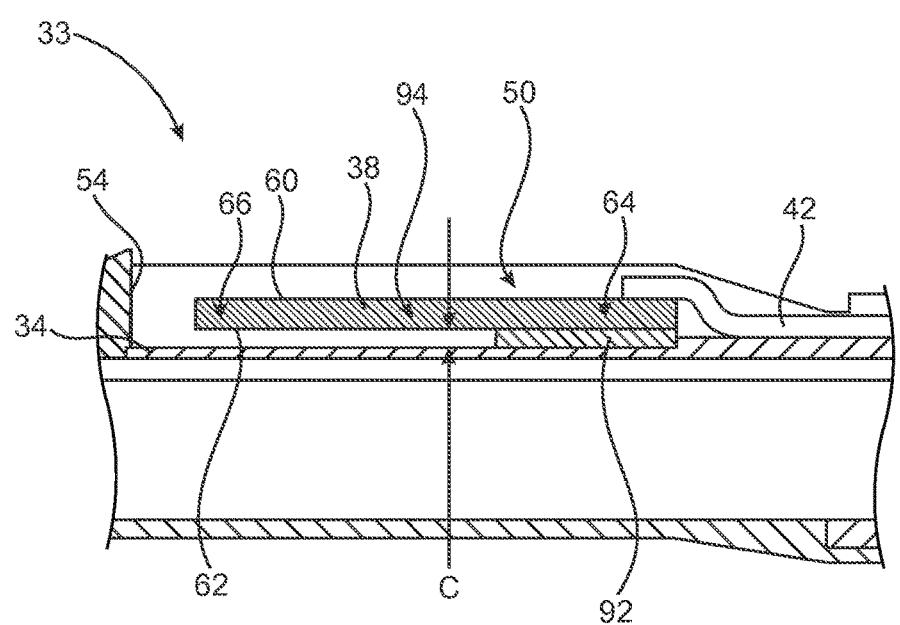
FIG. 10 illustrates a distal portion of yet another embodiment of the catheter of FIG. 1 in longitudinal cross-section.

FIG. 10 is an enlarged cross-sectional view of another embodiment of distal tip 33. In the embodiment of FIG. 10, distal tip 33 does not have interposer, sensor wires, a step formed into shaft wall 34, and sensor 38 has only an elongate portion, with no support portion as in FIG. 9. Second surface 62 of sensor 38 may be coupled to shaft wall 34 by an adhesive 92, such that the adhesive layer elevates the sensor 38 above shaft wall 34 creating a void between second surface 62 and shaft wall 34. In one embodiment as shown in FIG. 10, distance C, which is the distance adhesive 92 elevates sensor 38 above shaft wall 34, measures about 40 to 50 microns, or in another embodiment about 25-60 microns. Thus, in the embodiment of FIG. 10, the size of the void disposed between second surface 62 of sensor 38 and shaft wall 34 depends on the distance C or the thickness of adhesive layer 92. As a result, second surface 62 of sensor 38 is spaced apart from shaft wall 34 by having a void disposed between second surface 62 of sensor 38 and shaft wall 34. As previously described with reference to FIG. 6, second end 66 of sensor 38 may also be spaced apart from sidewall 54 of pocket 50 by having a void disposed between sensor 38 and sidewall 54 of pocket 50. With second end 66 spaced apart from shaft wall 34 and sidewall 54, at least a portion of sensor 38 may be exposed to the environment and first surface 60, second surfaces 62 and second end 66 could be surrounded by a fluid when catheter 10 is disposed within lumen 12 of vessel 14.

A method of measuring FFR using measurement catheter 100 will now be described with reference to FIG. 1. As would be understood by those skilled in the art, when measuring FFR a guide catheter (not shown) may be advanced through the vasculature such that the guide catheter is disposed within the aorta with a distal end thereof disposed within the aorta at an ostium of the aorta adjacent the branch vessel 14 within which lesion 16 is located. As shown in FIG. 1, guidewire 44 can be advanced intraluminally through the guide catheter, into vessel 14 within lumen 12 to the site of lesion 16. In the embodiment shown, guidewire 44 is advanced from proximal side 46 of lesion 16 to distal side 48 of lesion 16, which is also consistent with the direction of the blood flow BF, as indicated by the arrow BF in FIG. 1. In an embodiment, vessel 14 is a coronary artery, but vessel 14 may be other vessels in which it may be desirable to measure pressure, and in particular, to measure FFR.

Thereafter, as shown in FIG. 1, measurement catheter 10 can be tracked or advanced over indwelling guidewire 44 to the target site such that distal end 32 of elongate shaft 18 is positioned distal of lesion 48. As can be seen in FIG. 1, distal tip 33 including pressure sensor 33 can be disposed distally of lesion 16 such that elongate shaft 18 is disposed through lesion 16.

With measurement catheter 10 in place, pressure sensor 33 measures the pressure of blood distal of the lesion within lumen 12. Accordingly, the pressure measured by pressure sensor 33 is the distal pressure measurement, or $P_d$, used in calculating FFR. In one embodiment, adenosine is administered either intracoronary at the site, bolus, or intravenously by continuous infusion for providing an accurate distal pressure measurement ($P_d$) for an FFR value. A proximal pressure measurement $P_a$, which is taken in the aorta by an external AO pressure transducer associated with the guide catheter, and a simultaneous pressure measurement $P_d$ taken with pressure sensor 33 of measurement catheter 10 are then obtained to provide the FFR value, i.e., $P_d/P_a$, for the lesion. The proximal pressure measurement $P_a$ and distal pressure measurement $P_d$ can be communicated to computing device 40. Computing device 40, shown schematically in FIGS. 1 and 2, may include such components as a CPU, a display device, an amplification and filtering device, an analog-to-digital converter, and various other components. Computing device 40 may receive the proximal pressure measurement $P_a$ and distal pressure measurement $P_d$, and may process them to provide a continuous display of FFR measurement.

When the FFR measurement is completed, measurement catheter 10 may then be completely withdrawn from the patient or repositioned in vivo at another lesion and the process repeated. Pressure-sensing catheters in accordance with embodiments hereof may be used for other than providing proximal and distal pressure measurements ($P_a$, $P_d$) for calculating an FFR value. For instance, pressure-sensing catheters in accordance with embodiments hereof may be used to provide an in vivo pressure measurement anywhere along the vasculature, or a particular lesion therein. As well, embodiments hereof may be used to provide in vivo pressure measurements, across a heart valve, venous valve or other valvular location within the body where it may be deemed useful.

The detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as but not limited to peripheral arteries, carotid arteries, renal arteries, and/or venous applications. Furthermore, there is no intention to be bound by any expressed or implied theory presented in the preceding technical field, background, brief summary or the detailed description.

Further Examples

The following examples are illustrative of several embodiments of the present technology:

1. A catheter comprising:
an elongate shaft including a proximal portion and a distal portion extending from the proximal portion to a distal opening at a distal end of the shaft, the elongate shaft having a shaft wall, the shaft wall having an outer and inner surface, the shaft wall inner surface defining a guidewire lumen; and
a pressure sensor having a first end coupled to the shaft wall outer surface at the distal end of the elongate shaft, the pressure sensor having a second end not coupled to the elongate shaft, wherein the second end of the pressure sensor is spaced apart from the shaft wall outer surface, such that at least a portion of the pressure sensor is isolated from the bending stresses of the shaft wall when the elongate shaft is tracked to a treatment site within a vasculature.

2. The catheter of claim 1, wherein the sensor is disposed within a pocket on the distal end of the elongate shaft, the pocket defined by the shaft wall outer surface and at least one sidewall extending substantially perpendicular to the shaft wall.

3. The catheter of claim 2, wherein the pocket is exposed to the environment such that at least a portion of the sensor will be surrounded on all sides by a fluid when the elongate shaft is tracked within the vasculature.

4. The catheter of claim 2 or 3, wherein the second end of the sensor is spaced apart from the at least one sidewall.

5. The catheter of any of the preceding claims, further comprising an interposer disposed between the shaft wall and the first end of the sensor such that the interposer elevates the sensor above the shaft wall to create a void between the shaft wall and the sensor.

6. The catheter of any of the preceding claims, wherein a step is formed in the shaft wall adjacent the first end of the sensor such that the step elevates the sensor above the shaft wall to create a void between the shaft wall and the sensor.

7. The catheter of any of the preceding claims, wherein the sensor comprises a support portion adjacent the first end of the sensor, and an elongate portion, wherein the support portion is sized such that the support portion elevates the elongate portion of the sensor above the shaft wall to create a void between the shaft wall and the sensor. The catheter of any of the preceding claims, wherein a layer of adhesive is disposed between the shaft wall and the first end of the sensor such that the layer of adhesive elevates the sensor above the shaft wall to create a void between the shaft wall and the sensor.

9. A catheter comprising:
an elongate shaft including a proximal portion and a distal portion extending from the proximal portion to a distal opening at a distal end of the shaft, the elongate shaft having a shaft wall, the shaft wall having an outer and inner surface, the shaft wall inner surface defining a guidewire lumen;
an interposer having a first and second surface, wherein the interposer is mounted to the shaft wall outer surface on the interposer second surface; and
a pressure sensor having a first end coupled to the first surface of the interposer, wherein the second end of the pressure sensor is not coupled to the interposer or the shaft wall, the second end is spaced apart from the shaft wall outer surface, such that at least a portion of the pressure sensor is isolated from the bending stresses of the shaft wall when the elongate shaft is tracked to a treatment site within a vasculature.

10. The catheter of claim 9, wherein the shaft wall further defines a pressure sensor wire lumen, the interposer having communication wires coupled to the first surface wherein the communication wires extend proximally through the pressure sensor wire lumen, further wherein pressure sensor wires extend from the first surface of the interposer to the second end of the pressure sensor.

11. The catheter of claim 9 or 10, wherein the sensor and interposer are disposed within a pocket on the distal end of the elongate shaft, the pocket defined by the shaft wall outer surface and at least one sidewall extending substantially perpendicular to the shaft wall.

12. The catheter of claim 11, wherein the pocket is exposed to the environment such that at least a portion of the sensor will be surrounded on all sides by a fluid when the elongate shaft is tracked within the vasculature.

13. The catheter of claim 11 or 12, wherein the second end of the sensor is spaced apart from the at least one sidewall.

14. The catheter of any of claims 9 to 13, further comprising a layer of adhesive disposed between at least one of the pressure sensor, the interposer, and the shaft wall outer surface, such that the at least one layer further elevates the sensor above the shaft wall to create a void between the shaft wall and the sensor.

15. A catheter comprising:
an elongate shaft including a proximal portion and a distal portion extending from the proximal portion to a distal opening at a distal end of the shaft, the elongate shaft having a shaft wall, the shaft wall having an outer and inner surface, the shaft wall inner surface defining a guidewire lumen; and
a pressure sensor having a support portion and an elongate portion, the support portion coupled to the shaft wall outer surface at the distal end of the elongate shaft, wherein the elongate portion of the pressure sensor is spaced apart from the shaft wall outer surface, such that at least a portion of the pressure sensor is isolated from the bending stresses of the shaft wall when the elongate shaft is tracked to a treatment site within a vasculature.

16. The catheter of claim 1, wherein the sensor is disposed within a pocket on the distal end of the elongate shaft, the pocket defined by the shaft wall outer surface and at least one sidewall extending substantially perpendicular to the shaft wall.

17. The catheter of claim 16, wherein the pocket is exposed to the environment such that at least a portion of the sensor will be surrounded on all sides by a fluid when the elongate shaft is tracked within the vasculature.

18. The catheter of claim 16 or 17, wherein the elongate portion of the sensor is spaced apart from the at least one sidewall.

19. The catheter of any of claims 1 to 18, further comprising a layer of adhesive disposed between the support portion and the shaft wall outer surface such that the at least one layer of adhesive further elevates the sensor above the shaft wall to create a void between the shaft wall and the sensor.

While various embodiments according to the present invention have been described above, it should be understood that they have been presented by way of illustration and example only, and not limitation. It will be apparent to persons skilled in the relevant art that various changes in form and detail can be made therein without departing from the scope of the invention. Thus, the breadth and scope of the present invention should not be limited by any of the above-described exemplary embodiments. It will also be understood that each feature of each embodiment discussed herein, and of each reference cited herein, can be used in combination with the features of any other embodiment.

What is claimed is:

1. A catheter comprising:
an elongate shaft including a proximal portion and a distal portion extending from the proximal portion to a distal opening at a distal end of the shaft, the elongate shaft having a shaft wall, the shaft wall having an outer surface and an inner surface, the inner surface defining a guidewire lumen; and
a pressure sensor unitarily formed of a support portion and an elongate portion, the support portion coupled to the outer surface of the shaft wall at the distal end of the elongate shaft, wherein the support portion is sized such that the support portion elevates the elongate portion of the pressure sensor above the shaft wall to create a void between the outer surface of the shaft wall and the pressure sensor, such that at least a portion of the pressure sensor is isolated from the bending stresses of the shaft wall when the elongate shaft is tracked to a treatment site within a vasculature.

2. The catheter of claim 1, wherein the pressure sensor is disposed within a pocket on the distal end of the elongate shaft, the pocket defined by the outer surface of the shaft wall and at least one sidewall extending substantially perpendicular to the shaft wall.

3. The catheter of claim 2, wherein the pocket is exposed to the environment such that at least a portion of the pressure sensor will be surrounded on five sides by a fluid when the elongate shaft is tracked within the vasculature.

4. The catheter of claim 2, wherein the elongate portion of the pressure sensor is spaced apart from the at least one sidewall.

5. The catheter of claim 1, further comprising a layer of adhesive disposed between the support portion and the outer surface of the shaft wall such that the at least one layer of adhesive further elevates the pressure sensor above the shaft wall to create a void between the shaft wall and the pressure sensor.

\* \* \* \* \*